United States Patent
Halloran et al.

Patent Number: 5,194,251
Date of Patent: Mar. 16, 1993

[54] HAIR TREATMENT WITH ZWITTERIONOMERIC SILOXANES

[75] Inventors: Daniel J. Halloran, Midland; Terence J. Swihart, Essexville, both of Mich.

[73] Assignee: Dow Corning Corporation, Midland, Mich.

[21] Appl. No.: 833,252

[22] Filed: Feb. 10, 1992

[51] Int. Cl.$^5$ .......................... A61K 7/08; A61K 7/11
[52] U.S. Cl. ......................................... 424/70; 424/71
[58] Field of Search ................. 424/70; 556/425, 418, 556/419

[56] References Cited

U.S. PATENT DOCUMENTS

| | | | |
|---|---|---|---|
| 4,609,750 | 9/1986 | Kollmeier et al. | 556/419 |
| 4,918,210 | 4/1990 | Fenton et al. | 556/425 |
| 5,008,424 | 4/1991 | Halloran et al. | 556/418 |

Primary Examiner—Thurman K. Page
Assistant Examiner—D. Colucci
Attorney, Agent, or Firm—Jim L. DeCesare

[57] ABSTRACT

A method of treating hair in which a formulation is applied to the hair which includes an organosilicon compound. The improvement resides in incorporating into the formulation as the organosilicon compound an amine carboxylate zwitterionomeric polysiloxane having the formula

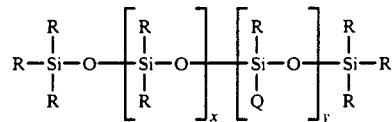

Q in the formula is preferably an organofunctional group represented by

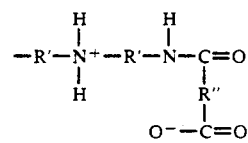

in which R' is an alkylene radical of from one to twelve carbon atoms; and R" is ethylene, vinylidene or phenylene.

20 Claims, No Drawings

HAIR TREATMENT WITH ZWITTERIONOMERIC SILOXANES

BACKGROUND OF THE INVENTION

This invention relates to a method of treating hair by applying thereto certain amine carboxylate zwitterionomeric polysiloxanes which have been found to impart conditioning benefits to hair.

Hair preparations are compositions which are employed on the scalp or hair. The most important hair preparations are shampoos, conditioning products, colorants, hairstyling preparations including setting lotions and hairsprays, and permanent wave preparations.

Shampoos are mild cosmetic products for cleaning the hair and scalp. Hair becomes soiled due to skin flakes, sebum, perspiration, dust, and residues from sprays, lotions and conditioning agents. Shampoos are designed to leave the hair clean, pliable, lustrous, possessing a pleasant odor, and easy to untangle, comb, manage, and style. The principal ingredient of a shampoo is a surfactant which functions to release dirt from the hair and to transport it to the aqueous Since consumers equate lathering with cleanliness, anionic surfactants such as alkyl sulfates and sulfonates are preferred because of their high lather. Numerous other constituents are included in shampoos such as thickeners to prevent the shampoo from running down the face into the eyes, opacifiers to provide a rich pleasing pearlescent appearance, buffers to adjust the pH of the shampoo to a value which is gentle to the skin, and fragrances to impart a pleasant aroma to the washed hair following rinsing. Most frequently, shampoos are marketed as clear products although gels having a higher viscosity and packaged in tubes, and pearlescent compositions are available. Exemplary shampoo formulations are described in detail in U.S. Pat. No. 4,364,837 issued Dec. 21, 1982; U.S. Pat. No. 4,704,272 issued Nov. 3, 1987; and U.S. Pat. No. 4,741,855 issued May 3, 1988.

With the advent of consumer trends toward daily hair washing, conditioning shampoos have emerged which are designed to render the hair easy to comb and tangle free in the wet state, as well as glossy and soft when dry. Such conditioning is provided by cationic polymers which upon rinsing produce a thin film on the hair. This film functions as a lubricant when the hair is wet and prevents static charge and "flyaway" when the hair is dry. Conditioning shampoos are described in U.S. Pat. No. 4,559,227 issued Dec. 17, 1985 and U.S. Pat. No. 4,777,037 issued Oct. 11, 1988.

Conditioning may also be provided by hair conditioning products designed solely for that purpose such as rinses, mousses, aerosols, and pump sprays, which conditioners are applied following shampooing. These conditioning products are rinsed from the hair a short time following their application. Such conditioners prevent excessive split ends and other mechanical hair damage and roughening, and seek to neutralize the adverse effects which hair undergoes due to humidity, temperature, exposure to sunlight, frequent washing, combing, and brushing, and cosmetic treatments such as bleaching, dyeing, and waving. Examples of these products can be found in U.S. Pat. No. 4,387,090 issued Jun. 7, 1983; U.S. Pat. No. 4,563,347 issued Jan. 7, 1986; and U.S. Pat. No. 4,954,335 issued Sep. 4, 1990.

Styling preparations are not rinsed out and remain in the hair. Such preparations contain film forming agents such as vinylpyrrolidone polymers and copolymers which are designed to stabilize the hairstyle during and following its creation with a comb, brush, or rollers. Setting lotions for temporary sets are applied to the hair after it has been washed and towel dried. The hair is then wound on rollers and dried. Setting lotions for blow drying are similarly applied but the hair is brushed and combed while being dried with a hair dryer. Stabilization of the hairstyle is achieved by stiffening and increased friction between hairs. These lotions are marketed as thin aqueous alcohol solutions, aerosol sprays, pump sprays, and aerosol foam mousses. Various hair setting formulations are set forth in U.S. Pat. No. 4,724,851 issued Feb. 16, 1988; U.S. Pat. No. 4,733,677 issued Mar. 29, 1988; and U.S. Pat. No. 4,834,968 issued May 30, 1989.

Hairsprays are used to protect the hair from wind and humidity. Such sprays should dry quickly and be easily removable by brushing and washing without generating a visible dust. The hair must have a pleasant smell, be glossy, and not feel dull following application. Typically, these formulations are marketed as two phase aerosols containing a film forming agent, a solvent, and a propellant. Ethanol is the preferred solvent, and since 1979 alternative hydrocarbon propellants such as propane, butane, isobutane, pentane, and dimethylether have replaced the chlorofluorocarbons. Packaging is an important aspect of hairsprays and metal containers having an inner coating of lacquer are required. The valve and nozzle selection for the container is crucial for provision of a proper spray pattern. More recent novel hairstyling preparations include setting gel fixatives which are thickened solutions and microemulsions containing film forming agents which provide for the creation of the "wetlook" hairstyle. Examples of hairspray products are described in U.S. Pat. No. 3,928,558 issued Dec. 23, 1975 and U.S. Pat. No. 4,871,529 issued Oct. 3, 1989.

The amine carboxylate zwitterionomeric polysiloxanes of the present invention may be employed in any of the foregoing hair treatment preparations for the purpose of imparting conditioning benefits. In addition to conditioning, it has been unexpectedly discovered that these zwitterionomers provide a body effect to the hair rendering it springy and bouncy. This is significant since known hair bodying agents are resins whereas the zwitterionomers of the present invention are fluids capable of forming elastomeric films.

While it is known to apply organosilicon ionomeric compounds to hair as shown in U.S. Pat. No. 4,609,750 issued Sep. 2, 1986, the amine carboxylate zwitterionomeric polysiloxanes of the present invention differ significantly from these betaines of the prior art.

For example, the ionomers of the present invention are ammonium carboxylate ionomers whereas the ionomers of the '750 patent are permanent quaternary amine carboxylate ionomers. Thus, the nitrogen atom in the '750 patent is always positively charged. Because of this permanent positive charge and because there are no hydrogen atoms bonded to the cationic site in the '750 patent as in the ionomers of the present invention, it is possible to form a multiplicity of structures with the ionomers of the present invention. In addition to the pure ionomer, the present invention provides for the formation of conjugate acid base pairs of the ionomer with either an acid or a base. Both pairs are not possible with the ionomers of the '750 patent.

An additional distinction between the ionomers of the present invention and the ionomers of the '750 patent is that the ionomers of the '750 patent are betaines and not amino acids, whereas the ionomers of the present invention can be appropriately classifiable as silicone functional amino acids. Finally, the order of arrangement of the amide linkage, the positive charge, and the negative charge, in the Q group of the '750 patent and the present invention is not the same. Specifically, the order of the positive charge and the amide linkage in these Q groups is reversed.

Alkyl betaines are also representative of zwitterions and are a special class of zwitterion but there is no hydrogen atom bonded to the cationic site. Some silicones are zwitterions and it is this special category of silicone zwitterion to which the present invention relates.

The zwitterionomeric aminofunctional siloxane compounds of the present invention may be prepared in accordance with the following reaction schematic:

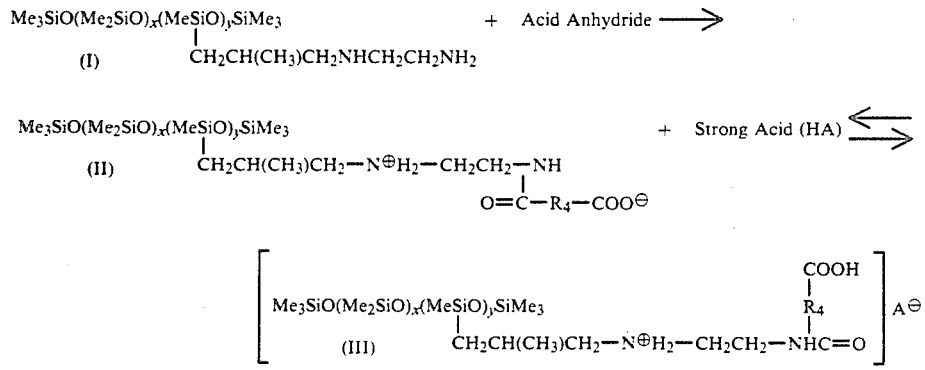

SUMMARY OF THE INVENTION

The invention is directed to a method of treating hair in which a formulation is applied to the hair which includes an organosilicon compound. The improvement resides in incorporating into the formulation as the organosilicon compound an amine carboxylate zwitterionomeric polysiloxane.

It is therefore an object of the present invention to provide a hair treatment method utilizing certain silicone zwitterionomers which have been found to function as bodying agents when applied to hair.

The advantages provided by the method of the present invention is the discovery that the silicone zwitterionomers described herein as a group exhibit good wet and dry combing characteristics as well as improved wet and dry feel. An additional and unexpected advantage is that hair treated with the disclosed zwitterionomers remains springy and bouncy following treatment indicating an improvement in hair body.

These and other objects, advantages and features of the herein described present invention will become more apparent when considered in light of the following detailed description thereof.

DETAILED DESCRIPTION OF THE INVENTION

A zwitterion is a molecule that exists as a dipolar ion rather than in the un-ionized form. The molecule is neutral overall but has a large charge separation like an amino acid. Zwitterions are also known as hybrid ions, and internal or intramolecular salts. In the case of amino acids, they are electrolytes having separated weakly acidic and weakly basic groups. For example, while shown as $H_2N-R-COOH$, in aqueous solution $^\oplus H_3N-R-COO^-$ is the actual species where an internal proton transfer from the acidic carboxyl to the basic amino site is complete. The uncharged species has separate cationic and anionic sites but the positive and the negative ions are not free to migrate. Thus, it is a complex ion that is both positively and negatively charged.

In the above schematic formula (I) denotes an aminofunctional siloxane, formula (II) denotes the zwitterionomer of the present invention, and formula (III) indicates the conjugate acid base pair of the zwitterionomer and the strong acid (HA).

Formula (I) is an aminofunctional siloxane selected from the group consisting of reaction products of (A) a blend or reaction product of a hydroxyl endblocked polydimethylsiloxane having a viscosity in the range of about 10 to 15,000 cs at twenty-five degrees centigrade, and a silane selected from the group consisting of those having the general formulae $R''_n(R'O)_{3-n}Si(CH_2)_3NHR'''$ and $R''_n(R'O)_{3-n}SiRNHCH_2CH_2NH_2$ wherein $R'''$ is a hydrogen atom or a methyl radical, $R''$ is a monovalent hydrocarbon radical free of aliphatic unsaturation and contains from one to six carbon atoms, n has a value of from zero to two, $R'$ is an alkyl radical containing from one to four carbon atoms, and R is a divalent hydrocarbon radical free of aliphatic unsaturation and contains three to four carbon atoms; (B) a blend or reaction product of a hydroxyl endblocked polydimethylsiloxane having a viscosity in the range of about 10 to 15,000 cs at twenty-five degrees centigrade, a silane selected from the group consisting of those having the general formulae $(R_1O)_3-SiR_2NHR_3$ and $(R_1O)_3-SiR_2NHCH_2CH_2NH_2$ wherein $R_1$ is an alkyl radical containing from one to four carbon atoms, $R_2$ is a divalent hydrocarbon radical free of aliphatic unsaturation and contains from three to four carbon atoms, and $R_3$ is selected from the group consisting of the hydrogen atom and the methyl radical, and a silane having the general formula $X_3SiZ$ wherein X is selected from the group consisting of alkoxy and acyloxy radicals containing from one to four carbon atoms, and Z is a nonhydrolyzable radical selected from the group consisting of hydrocarbon radicals, halogenated hydrocarbon radicals, and radicals composed of carbon, hydrogen, and oxygen atoms, wherein the oxygen atoms are present in hydroxyl groups, ester groups, or ether linkages, there being from one to ten carbon atoms in the Z radical; and (C) a blend or reaction product of a polydimethylsiloxane having a viscosity in the range of about one to 15,000 cs at twenty-five degrees centigrade, and a silane selected from the group consisting of those having the general formulae $R''_n(R'O)_{3-n}Si(CH_2)_3NHR'''$ and $R''_n(R'O)_{3-n}SiRNHCH_2CH_2NH_2$ wherein $R'''$ is a hydrogen atom or a methyl radical, $R''$ is a monovalent hydrocarbon radical free of aliphatic unsaturation and contains from one to six carbon atoms, n has a value of from zero to two, $R'$ is an alkyl radical containing from one to four carbon atoms, and R is a divalent hydrocarbon radical free of aliphatic unsaturation and contains three to four carbon atoms.

Such compositions are described in U.S. Pat. No. 3,508,933 issued Apr. 28, 1970; U.S. Pat. No. 3,836,371 issued Sep. 17, 1974; and U.S. Pat. No. 3,890,271 issued Jun. 17, 1975. The preparation of these compounds is detailed in the aforementioned patents, the disclosures of which are incorporated herein by reference thereto. Particular of the formula (I) compounds prepared and falling within the scope of the present invention is set forth in Table I.

TABLE I

| Compound (I) | x | y |
|---|---|---|
| A | 45.75 | 2.25 |
| B | 69.25 | 3.75 |
| C | 96 | 2 |
| D | 188 | 10 |
| E | 295.9 | 2.1 |
| F | 400 | 8 |

In the above reaction schematic, the acid anhydride which is reacted with compounds of formula (I) is one of succinic anhydride, maleic anhydride, phthalic anhydride, itaconic anhydride or other cyclic anhydrides; and carbon dioxide; with the first named anhydride being the preferred material.

The resulting reaction product indicated by formula (II) in the foregoing reaction schematic is an aminofunctional siloxane zwitterionomer having the structural formula:

$$Me_3SiO(Me_2SiO)_x(MeSiO)_ySiMe_3$$
$$|$$
$$CH_2CH(CH_3)CH_2\text{---}N^{\oplus}H_2\text{---}CH_2CH_2\text{---}NH$$
$$|$$
$$O=C\text{---}R_4\text{---}COO^{\ominus}$$

where Me is methyl; x is an integer of from about forty to about four hundred; y is an integer of from about one to about twenty; and $R_4$ is ethylene, vinylidene or phenylene.

The zwitterionic aminofunctional siloxane of formula (II) can be further reacted with a strong acid (HA) resulting in an equilibrium of the zwitterion (II) and a conjugate acid base pair indicated by formula (III) of the zwitterion (II) and the acid (HA) which depends upon the pKa of the strong acid and the dielectric strength of the solvent. The strong acid (HA) is one of hydrochloric, hydrobromic, hydriodic, nitric, perchloric, phosphoric; as well as organic acids such as acetic, propionic, butyric, valeric, caproic, benzoic, halo-substituted benzoic and nitro-substituted benzoic. The resulting formula (III) compound as shown above of the conjugate acid base pair of the zwitterion (II) and the strong acid (HA) has the structural formula:

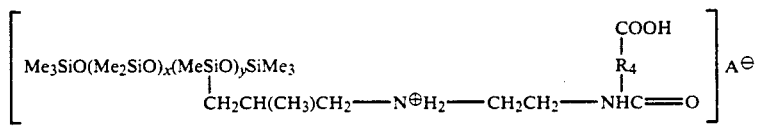

where Me is methyl; x is an integer of from about forty to about four hundred; y is an integer of from about one to about twenty; A is an anion; and $R_4$ is ethylene, vinylidene, or phenylene.

This is an alternative embodiment of the present invention, and it is not a requirement that the conjugate compound (III) be formed. However, it should be noted that where the conjugate (III) is formed, it necessitates the presence in the formulation of an acid. The equilibrium reached between the zwitterionomer (II) and the conjugate (III) depends on the strength of the acid. Where the acid is strong, the conjugate (III) predominates. Where the acid is weaker, the zwitterionomer predominates. As noted hereinbefore, such equilibrium depends upon the pKa of the strong acid and the dielectric strength of the solvent.

The zwitterionic aminofunctional siloxane of formula (II) may be reacted with a basic compound resulting in an equilibrium of the zwitterion (II) and a conjugate acid base pair indicated by formula (IV) of the zwitterion (II) and the basic compound B which depends upon the relative pKa's of the base B and the basic sites of the zwitterion, and the dielectric strength of the medium. The strong base is one of organic amines, hydroxides, and Lewis bases. The resulting formula (IV) compound as shown below of the conjugate acid base pair of the zwitterion (II) and the basic compound B has the structural formula:

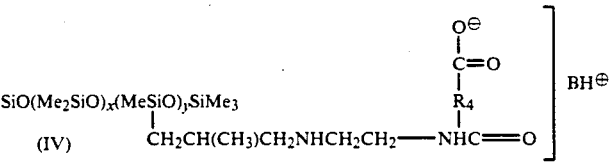

where Me is methyl; x is an integer of from about forty to about four hundred; y is an integer of from about one to about twenty; BH is a cation and a protonated base; and $R_4$ is ethylene, vinylidene, or phenylene.

This is another alternate embodiment of the present invention, and is not a requirement that the conjugate compound be formed. However, it should be noted that where the conjugate (IV) compound is formed, it necessitates the presence in the formulation of a basic compound such as dibutyl amine. The equilibrium reached between the zwitterionomer (II) and the conjugate (IV) depends on the strength of the base. Where the base is strong, the conjugate (IV) predominates. Where the base is weaker, the zwitterionomer predominates. Such equilibrium depends upon the relative pKa's of the strong base and zwitterion, and the dielectric strength of the solvent.

The aminofunctional siloxanes of formula (I) may be prepared by an alternate method from that set forth in U.S. Pat. No. 3,508,993; U.S. Pat. No. 3,836,371; and U.S. Pat. No. 3,890,271; which are aforementioned. In the alternate method, the starting material is methyldimethoxyethylenediaminoisobutyl silane of the formula:

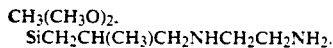

$CH_3(CH_3O)_2.$
$SiCH_2CH(CH_3)CH_2NHCH_2CH_2NH_2.$

This aminofunctional silane is distilled to an active concentration of between about 95-99%. The silane is hydrolyzed with three moles of water which are added to one mole of the silane. The material is batch distilled at atmospheric pressure and at a temperature of about one hundred and thirty degrees centigrade. Methanol and residual water are removed by vacuum stripping yielding the aminofunctional hydrolyzate. The aminofunctional hydrolyzate is added to a mixture of polydimethylsiloxane of viscosity of 1.5 centistokes; a dimethylcyclic siloxane of the formula $[(CH_3)_2SiO]_x$ where x is three, four, or five; and a catalyst such as potassium hydroxide or potassium silanolate. This mixture is equilibriated to a polymer by agitation and heating at about one hundred-fifty degrees centigrade. The mixture is cooled to about 80-90 degrees centigrade or lower and the catalyst is neutralized by the addition of acetic acid accompanied with mixing. The non-volatile content is increased by stripping of the volatile substances under vacuum, followed by filtration of the material in a pre-coated plate and frame filter for the purpose of removing any haze to obtain a clarified product. An example of this method is set forth below.

EXAMPLE I

Into a round bottom flask was added 3,482.8 grams of a dimethylcyclic siloxane, 439.2 grams of a hydrolyzed amine functional silane; 78.4 grams of polydimethylsiloxane of viscosity of 1.5 cs; and 38.3 grams of potassium silanolate catalyst. The contents of the flask were mixed under a nitrogen atmosphere for twenty minutes. Heat was applied to the flask and the contents were maintained at one hundred-fifty degrees centigrade for four hours. The mixture was cooled to thirty-three degrees centigrade. The catalyst was neutralized by the addition to the flask of 2.14 grams of acetic acid. The fluid was stirred overnight and filtered. The resulting product was water clear and had a viscosity of 354 cs. The product contained five mol percent amine and was identified as the material set forth in Table I where x=188 and y=10.

EXAMPLE II

Zwitterionic aminofunctional siloxane compounds of formula (II) were obtained by separately dissolving succinic anhydride in dimethoxyethane in order to provide a ten weight percent solution of the anhydride. The succinic anhydride was added from a dropping funnel to the contents of the flask of Example I containing the formula (I) aminofunctional siloxane. The solution was heated with stirring at about fifty-five degrees centigrade under a nitrogen flow. The mixture was vacuum distilled at about twenty millimeters of mercury under a nitrogen atmosphere at one hundred-twenty degrees centigrade for about forty-five minutes or until the vapor reached about eighty degrees centigrade, to remove all of the dimethoxyethane and yielding the zwitterionomer. The resulting zwitterionomer was distilled to a solids content of about eighty-eight percent. This example was repeated producing zwitterionomers having amine mol percentages ranging from about 0.5 mol percent to about eight mol percent.

The compositions of this invention may contain a surfactant selected from the group consisting of anionic and amphoteric surfactants. The surfactant system should provide an acceptable level of foam on the hair and be capable of cleaning the hair, and may comprise one or more water soluble detergents, i.e., an anionic or amphoteric surfactant. Suitable anionic detergents include sulfonated and sulfated alkyl, aralkyl and alkaryl anionic detergents; alkyl succinates; alkyl sulfosuccinates and N-alkyl sarcosinates. Especially preferred are the sodium, magnesium, ammonium, and the mono-, di- and triethanolamine salts of alkyl and aralkyl sulfates as well as the salts of alkaryl sulfonates. The alkyl groups of the detergents generally have a total of from about 12 to 21 carbon atoms, may be unsaturated, and are preferably fatty alkyl groups. The sulfates may be sulfate ethers containing one to ten ethylene oxide or propylene oxide units per molecule. Preferably, the sulfate ethers contain 2 to 3 ethylene oxide units.

Typical anionic detergents include, among others, sodium lauryl sulfate, sodium lauryl ether sulfate, ammonium lauryl sulfate, triethanolamine lauryl sulfate, sodium C14-16 olefin sulfonate, ammonium pareth-25 sulfate (ammonium salt of a sulfated polyethylene glycol ether of a mixture of synthetic C12-15 fatty alcohols), sodium myristyl ether sulfate, ammonium lauryl ether sulfate, disodium monooleamidosulfosuccinate, ammonium lauryl sulfosuccinate, sodium dodecylbenzene sulfonate, triethanolamine dodecylbenzene sulfonate and sodium N-lauroyl sarcosinate. The most preferred anionic detergents are the lauryl sulfates, particularly monoethanolamine, triethanolamine, ammonium and sodium lauryl sulfates. Sodium lauryl ether sulfate is also very suitable for use in the compositions of this invention.

Surfactants generally classified as amphoteric or ampholytic detergents include, among others, cocoamphocarboxyglycinate, cocoamphocarboxypropionate, cocobetaine, N-cocamidopropyldimethylglycine, and N-lauryl-N-carboxymethyl-N-(2-hydroxyethyl)ethylenediamine. Other suitable amphoteric detergents include the quaternary cycloimidates, betaines, and sultaines disclosed in U.S. Pat. No. 3,964,500. Particularly preferred amphoteric surfactants are the substituted quaternary hydroxy cycloimidinic acid alkali metal alcoholates described in U.S. Pat. No. 2,528,378.

The most preferred of the amphoteric surfactants are the substituted quaternary hydroxy cycloimidinic acid alkali metal alkoxymethyl carboxylates described in U.S. Pat. No. 2,781,354. The betaines may have the structure:

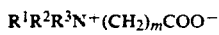

wherein $R^1$ is an alkyl group having about 12 to 18 carbon atoms or a mixture thereof, $R^2$ and $R^3$ are independently lower alkyl groups having 1 to 3 carbon atoms, and m is an integer from 1 to 4. Specific betaines useful in the products of the invention are for example alpha-(tetradecyldimethylammonio)acetate, beta-(hexadecyldiethylammonio)propionate, and gamma-(dodecyldimethylammonio)butyrate.

The sultaines may have the structure:

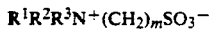

wherein $R^1$, $R^2$, $R^3$, and m are defined as above. Specific useful sultaines are for example 3-(dodecyldimethylammonio)-propane-1-sulfonate, and 3-(tetradecyldimethylammonio)ethane-1-sulfonate.

The compositions of this invention may contain a nonionic surfactant. The nonionic surfactants of the present invention are selected from the group consisting of fatty acid alkanolamide and amine oxide surfactants. The fatty acid alkanolamides are nonionic surfactants obtained by reacting alkanolamines such as monoethanolamine, diethanolamine, monoisopropanolamine, or diisopropanolamine with a fatty acid or fatty acid ester to form the amide. The hydrophobic portion of the nonionic surfactant is provided by a fatty acid hydrocarbon chain which generally has from 10 to 21 carbon atoms. The fatty acid alkanolamide surfactants include, for example, fatty acid diethanolamides such as isostearic acid diethanolamide, lauric acid diethanolamide, capric acid diethanolamide, coconut fatty acid diethanolamide, linoleic acid diethanolamides, myristic acid diethanolamide, oleic acid diethanolamide, and stearic acid diethanolamide; fatty acid monoethanolamides such as coconut fatty acid monoethanolamide; and fatty acid monoisopropanolamides such as oleic acid monoisopropanolamide and lauric acid monoisopropanolamide.

The amine oxides are well known nonionic surfactants usually obtained by oxidizing a tertiary amine to form the amine oxide. They are sometimes also referred to as polar nonionic surfactants. Amine oxide surfactants include, for example, the N-alkyl amine oxides such as N-cocodimethylamine oxide, N-lauryl dimethylamine oxide, N-myristyl dimethylamine oxide, and N-stearyl dimethylamine oxide; the N-acyl amine oxides such as N-cocamidopropyl dimethylamine oxide and N-tallowamidopropyl dimethylamine oxide; and N-alkoxyalkyl amine oxides such as bis(2-hydroxyethyl) $C_{12-15}$ alkoxy-propylamine oxide. The hydrophobic portion of the amine oxide surfactants is generally provided by a fatty hydrocarbon chain containing from 10 to 21 carbon atoms.

For purposes of this invention the alkanolamide and amine oxide surfactants are preferred. In general, the fatty acid diethanolamides and N-alkyl dimethylamine oxides are preferred for use in the compositions. Especially preferred are the fatty acid diethanolamides and N-alkyl dimethylamine oxides where the fatty hydrocarbon chain contains from 10 to 18 carbon atoms. For example, especially preferred nonionic surfactants include lauric acid diethanolamide, N-lauryl dimethylamine oxide, coconut acid diethanolamide, myristic acid diethanolamide, and oleic acid diethanolamide.

Additional categories of surfactant materials may also be included such as cationic and zwitterionic surfactants, and representative compounds are set forth in detail in U.S. Pat. No. 4,902,499, issued Feb. 20, 1990, which is considered to be incorporated herein by reference.

Other adjuvants may be added to the compositions of this invention such as thickeners, perfumes, colorants, electrolytes, pH control ingredients, antimicrobials, antioxidants, ultraviolet light absorbers and medicaments. For example, it is sometimes preferred to employ a thickener in the compositions to facilitate the hand application of the composition to the hair. Thickeners are preferably used in sufficient quantities to provide a convenient viscosity. For example, viscosities within the range of 400 to 6000 cps or more preferably in the range of 1000 to 4000 cps as measured at 25° C. are usually suitable.

Suitable thickeners, include, among others, sodium alginate, gum arabic, polyoxyethylene, guar gum, hydroxypropyl guar gum, cellulose derivatives such as methylcellulose, methylhydroxypropylcellulose, hydroxypropylcellulose, polypropylhydroxyethylcellulose, starch and starch derivatives such as hydroxyethylamylose, and starch amylose, locust bean gum, electrolytes such as NaCl, saccharides such as fructose and glucose, and derivatives of saccharides such as PEG-120 methyl glucose dioleate. Preferred thickeners include the cellulose derivatives and saccharide derivatives. The glucose derivative, PEG-120 methyl glucose dioleate, is especially preferred in the present invention.

The perfumes which can be used in the compositions are the cosmetically acceptable perfumes. Colorants are used to confer a color to the composition and may generally be used. Although not required, it is preferred to employ an acid to adjust the pH within the range of 5 to 9 or more preferably within the range of 6 to 8 in the compositions of this invention. Any water soluble acid such as a carboxylic acid or a mineral acid is suitable. For example, suitable acids include mineral acids such as hydrochloric, sulfuric, and phosphoric, monocarboxylic acids such as acetic acid, lactic acid, or propionic acid; and polycarboxylic acids such as succinic acid, adipic acid and citric acid.

If for special purposes conditioners are desired, they may be added. For example, any of the well-known organic cationic hair conditioning components may be added. Some cationic conditioning components that may be used in the present invention to provide hair grooming include quaternary nitrogen derivatives of cellulose ethers, homopolymers of dimethyldiallylammonium chloride, copolymers of acrylamide and dimethyldiallylammonium chloride, homopolymers or copolymers derived from acrylic acid or methacrylic acid containing cationic nitrogen functional groups attached to the polymer via ester or amide linkages, polycondensation products of N,N'-bis-(2,3-epoxypropyl)-piperazine or of piperazine-bis-acrylamide and piperazine, poly-(dimethylbutenylammonium chloride)-α,ω-bis-(triethanol-ammonium) chloride, and copolymers of vinylpyrrolidone and acrylic acid esters with quaternary nitrogen functionality. The above cationic organic polymers and others are described in more detail in U.S. Pat. No. 4,240,450 which is hereby incorporated by reference to further describe the cationic organic polymers. Other categories of conditioners may also be employed.

A preservative may be required and representative preservatives which may be employed include about 0.1–0.2 weight percent of compounds such as formaldehyde, dimethyloldimethylhydantoin, 5-bromo-5-nitro-1,3-dioxane, methyl-and propyl para-hydroxybenzoates, and mixtures of such benzoates with sodium dehydroacetate, sorbic acid, and imidazolidinyl urea.

The compositions of the present invention may also be formulated to include dyes, colorants, reducing agents, neutralizing agents, and preservatives, necessary for their application as permanent wave systems or hair dyes for example. The active formulation can be applied in several different forms including lotions, gels, mousses, aerosols, and pump sprays, for example, and as conditioners and shampoos. The active ingredient may include a carrier, and suitable carrier fluids for hair care formulations are water as well as, for example, such fluids as alcohols namely ethanol or isopropanol, hydrocarbons and halogenated hydrocarbons as mineral spirits and trichloroethane, cyclic siloxanes, and aerosol propellants.

When the composition is intended for aerosol application, propellant gases can be included such as carbon dioxide, nitrogen, nitrous oxide, volatile hydrocarbons such as butane, isobutane, or propane and chlorinated or fluorinated hydrocarbons such as dichlorodifluoromethane and dichlorotetrafluoroethane or dimethylether.

The preferred carrier for use in accordance with the present invention is a methylsiloxane fluid corresponding to the average unit formula $(CH_3)_aSiO_{(4-a/2)}$ wherein a is an integer having an average value of from two to three. The methylsiloxane fluid comprises siloxane units joined by Si-O-Si bonds. Representative units are $(CH_3)_3SiO_{\frac{1}{2}}$, $(CH_3)_2SiO_{2/2}$, $(CH_3)SiO_{3/2}$, and $SiO_{4/2}$. These units are present in such molar amounts so that there is an average of from about two to three methyl groups per silicon atom in the methylsiloxane fluid, and the fluid has a viscosity of less than about one hundred centistokes measured at twenty-five degrees Centigrade.

Preferably, the methylsiloxane fluid contains dimethylsiloxane units and optionally trimethylsiloxane units. Of particular utility are methylsiloxane fluids having a viscosity of less than about ten centistokes such as cyclopolysiloxanes of the general formula $[(CH_3)_2SiO]_x$ and linear siloxanes of the general formula $(CH_3)_3SiO[(CH_3)_2SiO]_ySi(CH_3)_3$ in which x is an integer having a value of from three to ten and y is an integer having a value of from zero to about four.

Thus, the low viscosity methylsilicone fluid contemplated in accordance with the present invention includes methylsiloxane fluids representative of which are volatile cyclic silicone fluids and volatile linear silicone fluids. Specific examples of these volatile methylsiloxane fluids are polydimethylcyclosiloxane and the linear silicone fluid hexamethyldisiloxane. Such volatile fluids have viscosities generally less than about ten centistokes measured at twenty-five degrees Centigrade and most preferably have viscosities between about 0.65 to 5.0 centistokes.

The volatile cyclic silicones generally conform to the formula $(R_2SiO)_x$ in which R is an alkyl radical having from one to three carbon atoms or a phenyl group. Most typically the cyclic siloxanes have the formula $[(CH_3)_2SiO]_x$ in which x is an integer from three to ten.

Some representative volatile cyclic siloxane compounds found to be especially useful in accordance with the present invention are the methylsiloxane tetramer octamethylcyclotetrasiloxane and the methylsiloxane pentamer decamethylcyclopentasiloxane. Mixtures of the tetramer and pentamer may also be employed. Such cyclic siloxanes have viscosities ranging from about 2.5 centistokes to about five centistokes. These materials are also known under The Cosmetics, Toiletries and Fragrance Association, Inc. monographic designation as cyclomethicone.

The volatile low viscosity linear methylsilicone fluid has the formula $R_3SiO(R_2SiO)_nSiR_3$ in which R is an alkyl radical having one to six carbon atoms and n is an integer of from two to nine. Most representative of this class of volatile linear methylsiloxane fluid is hexamethyldisiloxane of the formula

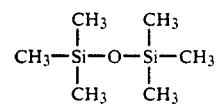

which has a viscosity of 0.65 centistokes measured at twenty-five degrees Centigrade.

Both the cyclic and linear low viscosity volatile methylsiloxane materials are clear fluids and are essentially odorless, nontoxic, nongreasy and nonstinging. Cosmetically these methylsiloxane fluids are nonirritating to the skin and exhibit enhanced spreadability and ease of rub-out when applied to skin tissue. Once applied, the materials will evaporate leaving behind no residue.

The method of treating hair in accordance with the present invention involves treating hair in which a formulation is applied to the hair which includes an organosilicon compound. The improvement relates to the incorporation into the formulation as the organosilicon compound an amine carboxylate zwitterionomeric polysiloxane having the formula

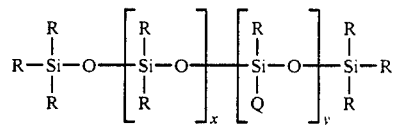

in which R is an alkyl radical having from one to six carbon atoms or a phenyl radical; x is an integer having a value of from forty to four hundred; y is an integer having a value of from one to twenty; and Q is an organofunctional group. The organofunctional group Q has a formula selected from the group consisting of

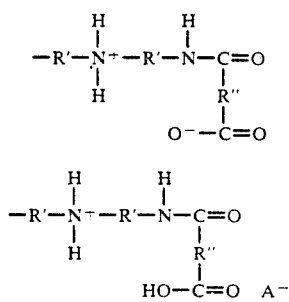

-continued

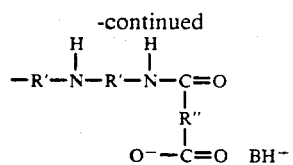

in which R' is an alkylene radical of from one to twelve carbon atoms; R" is ethylene, vinylidene or phenylene; A is an anion; and BH is a cation and a protonated base.

Preferably, the formulation is applied to the hair in the form of a solution of the organosilicon compound dissolved in a carrier. The solution should include from one to ten percent by weight of the organosilicon compound in the carrier. Most preferably, the solution includes about five percent by weight of the organosilicon compound in the carrier. In addition, the organosilicon compound should include from 0.4–8.0 mole percent of the organofunctional group Q. Most preferably, the organosilicon compound includes from 0.5–5.0 mole percent of the organofunctional group Q. As noted above, the preferred carrier is a methylsilicone fluid having a viscosity of less than about ten centistokes and having a formula selected from the group consisting of $[(CH_3)_2SiO]_x$ and $(CH_3)_3SiO[(CH_3)_2SiO]_ySi(CH_3)_3$ in which x is an integer having a value of from three to ten and y is an integer having a value of from zero to about four.

The invention is further illustrated with reference to the following example.

EXAMPLE III

Three zwitterionomeric siloxanes prepared in accordance with Example II were each formulated into a solution containing five percent by weight of the zwitterionomer in a cyclic siloxane as the carrier. The first zwitterionomer contained five mole percent of the organofunctional group Q and had a degree of polymerization of two hundred; the degree of polymerization being the length of the polymer chain indicated in terms of the number of repeat units in the chain. The second zwitterionomer contained 0.5 mole percent of the organofunctional group Q and had a degree of polymerization of four hundred. The third zwitterionomer contained two mole percent of the organofunctional group Q and had a degree of polymerization of one hundred. Each solution was applied to a 1.5 gram hair tress in an amount of 0.2 grams. The solution was rubbed into the tress and combed. The tress was dried employing a hair dryer and recombed. Wet combing, wet feel and dry combing were noted during each step. A tress treated with a solution having no zwitterionomer and a tress treated with a commercially available fixative formulation were employed as controls. The observed combing and tactile properties of the tresses treated with these solutions is set forth in Table II. Wet and dry combing were evaluated on a scale of one to five with one being the best and five being the worst.

TABLE II

| Content of Solution | DP | Mole % Q | Wet Combing | Dry Combing | Wet Feel |
|---|---|---|---|---|---|
| zwitterionomer | 200 | 5.0 | — | 2.0 | — |
| zwitterionomer | 400 | 0.5 | 1 | 1.5 | slippery |
| zwitterionomer | 100 | 2.0 | 2 | 1.5 | slippery |
| no silicone | — | — | — | 4.0 | — |
| commercial | — | — | — | 5.0 | — |

Table II indicates that the silicone zwitterionomers function as conditioning agents when applied to hair and hence have utility as conditioning additives in hair treatments. Unexpectedly it was found that tresses treated with the 100 and 400 DP zwitterionomer solutions remained springy and bouncy following the treatment indicating improved hair body affect. As noted above, this is a surprising property for materials which are fluids and not resins. The zwitterionomer solutions as a group also exhibited good wet and dry combing characteristics as well as improved wet and dry feel. The add-on level of the zwitterionomers was determined to be about fifteen percent of the hair weight by mass.

It will be apparent from the foregoing that many other variations and modifications may be made in the compounds, compositions and methods described herein without departing substantially from the essential features and concepts of the present invention. Accordingly, it should be clearly understood that the forms of the invention described herein are exemplary only and are not intended as limitations on the scope of the present invention as defined in the appended claims.

That which is claimed is:

1. In a method of treating hair in which a formulation is applied to the hair which includes an organosilicon compound, the improvement which comprises incorporating into the formulation as the organosilicon compound an amine carboxylate zwitterionomeric polysiloxane having the formula

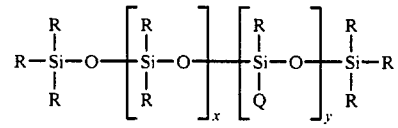

in which R is an alkyl radical having from one to six carbon atoms or a phenyl radical; x is an integer having a value of from forty to four hundred; y is an integer having a value of from one to twenty; and Q is

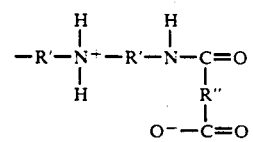

in which R' is an alkylene radical of from one to twelve carbon atoms; R" is ethylene, vinylidene or phenylene; the polysiloxane having a degree of polymerization of at least about one hundred.

2. The method of claim 1 in which the formulation is applied to the hair in the form of a solution of the organosilicon compound dissolved in a carrier.

3. The method of claim 2 in which the solution includes from one to ten percent by weight of the organosilicon compound in the carrier.

4. The method of claim 3 in which the solution includes about five percent by weight of the organosilicon compound in the carrier.

5. The method of claim 1 in which the organosilicon compound includes from 0.5–8.0 mole percent of the organofunctional group Q.

6. The method of claim 5 in which the organosilicon compound includes from 0.5–5.0 mole percent of the organofunctional group Q.

7. The method of claim 2 in which the carrier is a methylsilicone fluid having a viscosity of less than about ten centistokes and having a formula selected from the group consisting of [(CH₃)₂SiO]ₓ and (CH₃)₃Si-O[(CH₃)₂SiO]ᵧSi(CH₃)₃ in which x is an integer having a value of from three to ten and y is an integer having a value of from zero to about four.

8. In a method of treating hair in which a formulation is applied to the hair which includes an organosilicon compound, the improvement which comprises incorporating into the formulation as the organosilicon compound an amine carboxylate zwitterionomeric polysiloxane having the formula

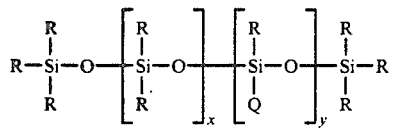

in which R is an alkyl radical having from one to six carbon atoms or a phenyl radical; x is an integer having a value of from forty to four hundred; y is an integer having a value of from one to twenty; and Q is

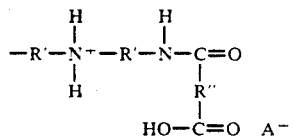

in which R' is an alkylene radical of from one to twelve carbon atoms; R" is ethylene, vinylidene or phenylene; A is an anion; the polysiloxane having a degree of polymerization of at least one hundred.

9. The method of claim 8 in which the formulation is applied to the hair in the form of a solution of the organosilicon compound dissolved in a carrier.

10. The method of claim 9 in which the solution includes from one to ten percent by weight of the organosilicon compound in the carrier.

11. The method of claim 8 in which the organosilicon compound includes from 0.5-8.0 mole percent of the organofunctional group Q.

12. The method of claim 9 in which the carrier is a methylsilicone fluid having a viscosity of less than about ten centistokes and having a formula selected from the group consisting of [(CH₃)₂SiO]ₓ and (CH₃)₃Si-O[(CH₃)₂SiO]ᵧSi(CH₃)₃ in which x is an integer having a value of from three to ten and y is an integer having a value of from zero to about four.

13. In a method of treating hair in which a formulation is applied to the hair which includes an organosilicon compound, the improvement which comprises incorporating into the formulation as the organosilicon compound an amine carboxylate zwitterionomeric polysiloxane having the formula

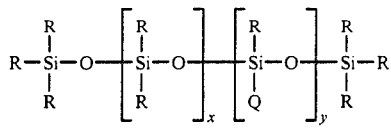

in which R is an alkyl radical having from one to six carbon atoms or a phenyl radical; x is an integer having a value of from forty to four hundred; y is an integer having a value of from one to twenty; and Q is

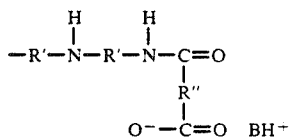

in which R' is an alkylene radical of from one to twelve carbon atoms; R" is ethylene, vinylidene or phenylene; BH is a cation and a protonated base; the polysiloxane having a degree of polymerization of at least one hundred.

14. The method of claim 13 in which the formulation is applied to the hair in the form of a solution of the organosilicon compound dissolved in a carrier.

15. The method of claim 14 in which the solution includes from one to ten percent by weight of the organosilicon compound in the carrier.

16. The method of claim 13 in which the organosilicon compound includes from 0.5-8.0 mole percent of the organofunctional group Q.

17. The method of claim 14 in which the carrier is a methylsilicone fluid having a viscosity of less than about ten centistokes and having a formula selected from the group consisting of [(CH₃)₂SiO]ₓ and (CH₃)₃Si-O[(CH₃)₂SiO]ᵧSi(CH₃)₃ in which x is an integer having a value of from three to ten and y is an integer having a value of from zero to about four.

18. The method of claim 1 in which the formulation is rubbed into the hair and combed after being applied, the hair is dried and the dried hair is recombed.

19. The method of claim 8 in which the formulation is rubbed into the hair and combed after being applied, the hair is dried and the dried hair is recombed.

20. The method of claim 13 in which the formulation is rubbed into the hair and combed after being applied, the hair is dried and the dried hair is recombed.

* * * * *